(12) United States Patent
Crook et al.

(10) Patent No.: US 7,326,406 B2
(45) Date of Patent: *Feb. 5, 2008

(54) DUAL COMPONENT SKIN CARE COMPOSITIONS THAT COMPRISE A SELF-TANNING AGENT

(75) Inventors: Teresa Barbara Crook, Camberley (GB); Alison Fiona Stephens, Cookham (GB)

(73) Assignee: The Procter & Gamble Company, Cincinnati, OH (US)

( * ) Notice: Subject to any disclaimer, the term of this patent is extended or adjusted under 35 U.S.C. 154(b) by 705 days.

This patent is subject to a terminal disclaimer.

(21) Appl. No.: 10/883,616

(22) Filed: Jul. 1, 2004

(65) Prior Publication Data

US 2005/0002978 A1 Jan. 6, 2005

(30) Foreign Application Priority Data

Jul. 3, 2003 (EP) .................................. 03254235

(51) Int. Cl.
- *A61Q 17/04* (2006.01)
- *A61Q 19/04* (2006.01)
- *A61Q 19/00* (2006.01)
- *A61K 8/02* (2006.01)

(52) U.S. Cl. .......................... 424/59; 424/60; 424/400; 424/401

(58) Field of Classification Search .................. 424/59, 424/60, 400, 401
See application file for complete search history.

(56) References Cited

U.S. PATENT DOCUMENTS 6,531,116 B1 3/2003 Suares et al.

FOREIGN PATENT DOCUMENTS

| CA | 1311688 | 12/1992 |
|---|---|---|
| DE | 44 41 470 A | 6/1995 |
| EP | 0 456545 B1 | 11/1991 |
| EP | 0 500446 B1 | 8/1992 |
| WO | WO 94/04130 A1 | 3/1994 |
| WO | WO 94/13258 A1 | 6/1994 |
| WO | WO 94/22419 A1 | 10/1994 |
| WO | WO 00/62740 A | 10/2000 |
| WO | WO 01/00164 A | 1/2001 |

*Primary Examiner*—Shelley A. Dodson
(74) *Attorney, Agent, or Firm*—Eric T. Addington; John M. Howell; Brian M. Bolam

(57) ABSTRACT

Cosmetic kits comprising at least two separated components are provided. The at least two separated components comprise, in one component, a self-tanning agent, and in the other, a reactive skin care active. The cosmetic kits provide increased skin health benefits when both components are applied to the skin simultaneously or successively.

17 Claims, No Drawings

DUAL COMPONENT SKIN CARE COMPOSITIONS THAT COMPRISE A SELF-TANNING AGENT

TECHNICAL FIELD

The present invention relates to dual component cosmetic kits. More specifically, cosmetic kits are provided comprising a self-tanning agent and a reactive skin care active in at least two separate components. The cosmetic kits herein provide improved stability and acute skin colour enhancement in combination with improved delivery of reactive skin care actives following topical application.

BACKGROUND

A wide variety of cosmetic compositions containing self-tanning agents have been used to increase the pigmentation of the skin. These compositions have been used to create artificial tans, bronzing the skin in a similar fashion to exposure to the sun. It would be preferable to incorporate skin care actives in self-tanning compositions to improve skin health whilst imparting colour. The self-tanning agents present in these compositions are typically quite unstable. This is thought to be due to the highly reactive nature of the self-tanning agents and/or the low pH that such products require. Degradation of the self-tanning agents with skin care actives in the formulation generally results in a reduction of available levels of self-tanning agent, and the production of undesirable colouring in the neat product during storage.

WO 94/04130, WO 94/13258, and WO 94/22419 disclose apparatus and methods for sunless tanning comprising an apparatus having two receptacles, one receptacle containing a fluid comprising dihydroxyacetone, the other receptacle containing a fluid formulation comprising respectively, primary amines, secondary polyamines, and amino acids, and dispensing means for simultaneously or sequentially providing desired amounts of the two fluids. However, the materials present in the second receptacle are secondary tanning agents or colour enhancers, and not ideal as skin care actives providing skin health benefits.

It is therefore desirable to provide cosmetic kits that colour or impart a natural-looking tan to the skin whilst simultaneously delivering skin actives to the skin, without unacceptable dicolouration of the product during storage, and without requiring high levels of the self-tanning agents or the skin care actives themselves.

SUMMARY

According to the present invention, cosmetic kits are provided comprising at least two separated components (a) and (b) intended to be mixed at the time of use or to be applied successively wherein component (a) comprises a self-tanning agent comprising an α-hydroxyaldehyde conforming to the formula;

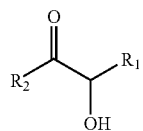

wherein $R_1$ is H, $CH_2OH$, $CHOHCH_2OH$, $CH(OH)CH(=O)$, $CH(OCH_3)CH(=O)$, $CH(NH_2)CH(=O)$, or $CH(NH\text{-Phenyl})CH(=O)$; and $R_2$ is H or $CH_2OH$; and component (b) comprises a reactive skin care active comprising vitamin $B_3$ or its derivatives, panthenol or its derivatives, dialkanol hydroxyproline compounds, hexamidine compounds, sugar amines or mixtures thereof.

DETAILED DESCRIPTION

All weights, measurements and concentrations herein are measured at 25° C. on the composition in its entirety, unless otherwise specified.

Unless otherwise indicated, all percentages of compositions referred to herein are weight percentages of the final composition (i.e. the sum of all components present) in the cosmetic kit and all ratios are weight ratios.

Unless otherwise indicated, all molecular weights are weight average molecular weights.

Unless otherwise indicated, the content of all literature sources referred to within this text are incorporated herein in full by reference.

Except where specific examples of actual measured values are presented, numerical values referred to herein should be considered to be qualified by the word "about".

The term "safe and effective amount" as used herein, means an amount of an active ingredient high enough to modify the condition to be treated or to deliver the desired skin care benefit, but low enough to avoid serious side effects, at a reasonable benefit to risk ratio within the scope of sound medical judgment. What is a safe and effective amount of the active ingredient will vary with the specific active, the ability of the active to penetrate through the skin or hair, the age, health condition, and skin or hair condition of the user, and other like factors.

As used herein, "cosmetically acceptable" means that ingredients which the term describes are suitable for use in contact with the skin or hair of humans and lower animals without undue toxicity, incompatibility, instability, irritation, allergic response and the like.

As used herein, the term "applied successively" means that the components of the present invention are dispensed and applied one after the other, the order of dispensing not being limited, such that component (a) can be dispensed either before or after component (b). Furthermore, the at least two components of the present invention may be dispensed and applied successively without directly following on from one another temporally, such that other components may be dispensed and applied at points before or after the first application of one of the at least two components, provided that the successive application of components (a) and (b) occurs within less than 2 hours of each other, preferably less than 1 hour, more preferably less than 30 minutes.

The cosmetic kit of the present invention comprises at least two components (a) and (b) that are stored separately, and intended to be mixed at the time of use, or to be applied successively to the skin. For the purposes of the present invention, the at least two components are given the designations component (a) and component (b). These designations are not intended to be limiting, such as for example indicating the order of application of the components. The designations are intended to indicate the two separate components and the constituents thereof.

In order to facilitate the separate storage of the at least two components, the cosmetic kit of the present invention may comprise at least one package for separately storing the at least two components. These packages are typically known to one skilled in the art as "dual chamber" packages.

Non-limiting examples of packaging suitable for use herein include an integral package comprising at least two compartments divided by separating means, one compartment comprising component (a) and the other comprising component (b). The separating means for keeping the two components apart may comprise a physical barrier such as a septum, or other similar barrier that prevents mixing of the two components from the at least two compartments known to those skilled in the art. Non-limiting examples of such packages include tubes comprising an exterior wall defining the outer surface of the tube and an inner void, and an interior septum, dividing the inner void into two compartments along its longitudinal axis such that the two components are kept separate until dispensed. Non-limiting examples of commercially available integral dual chamber packages comprising two separated compartments include dual chamber packages available from Airspray and Megaplast, and dual chamber tubes available from Cebel.

The cosmetic kit of the present application may comprise at least two packages, with component (a) being stored in one package, and component (b) in the other. The packages may be of similar design, or of different design. As is known to those skilled in the art, the package design will somewhat depend upon the product form, such that lotions and creams may be packaged in flexible or rigid-walled packages, whilst aerosol compositions typically are stored in rigid-walled, pressurised packages.

According to the present invention, component (a) comprises a self-tanning agent. As used herein, the term "self-tanning agent" includes α-hydroxy aldehydes and ketones such as dihydroxyacetone and structurally related compounds. This definition includes all such agents that are similarly useful in producing or inducing the artificial tanning process in human skin. Accordingly, the compositions of the present invention comprise an α-hydroxy aldehyde or ketone of the formula (I):

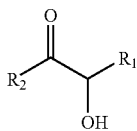

(I)

wherein $R_1$ is H, $CH_2OH$, $CHOHCH_2OH$, $CH(OH)CH(=O)$, $CH(OCH_3)CH(=O)$, $CH(NH_2)CH(=O)$, or $CH(NH\text{-Phenyl})CH(=O)$; and $R_2$ is H or $CH_2OH$. Dihydroxyacetone (DHA) itself may be represented by the following general structural formula:

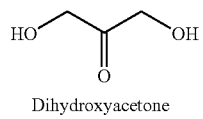

Dihydroxyacetone

A number of other compounds are already known in the art as capable of producing or inducing the same artificial tanning process in human skin as is produced or induced by DHA. Some of these are structurally similar to DHA, and include the following:

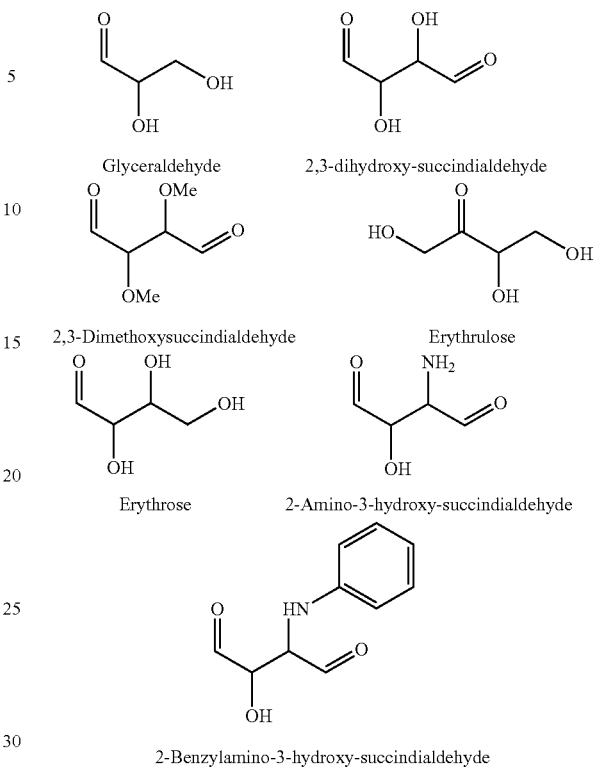

Preferably, the self-tanning agent comprises DHA, erythrulose, or mixtures thereof, more preferably DHA. Preferably the compositions of the present invention comprise from 0.01% to 10% of the self-tanning agent by weight of the total composition. More preferably, the compositions of the present invention comprise from 0.05% to less than 5%, more preferably still from 0.1% to 3.5%, and even more preferably from 0.1% to 2.5% of the self-tanning agent by weight of the final composition.

The cosmetic kits of the present invention comprise at least a second component, component (b). Component (b) comprises a reactive skin care agent. As used herein, the term "reactive skin care agent" includes materials that react with the self-tanning agent present in component (a) when present in the same phase, producing discolouration in the phase, and reducing the available levels of active self-tanning agent and reactive skin care agent present in the composition. It has surprisingly been found that these ingredients, when formulated in the same phase as the self-tanning agent, compromise the stability of the self-tanning agent and the composition as a whole. Without wishing to be bound by theory, it is believed that these reactive skin care agents either react directly with the self-tanning agent, degrading both themselves and the self-tanning agent in the process, or catalyse the auto-degradation of the self-tanning agent by promoting the formation of unstable dicarbonyl intermediates. This effectively lowers the amount of free, active self-tanning agent and reactive skin care active available in the composition. In order to overcome this, it is typically required to increase the levels of either one, or both, of these ingredients to ensure that enough active is applied to the skin in order to be effective. However, it has been found that this solution can be expensive, and may result in the composition discolouring to a greater extent, due to the formation of coloured reaction products that are generally undesirable for the consumer. It is desirable for self-tanning compositions to comprise these reactive skin care agents as when applied to the skin, they act synergistically with the self-tanning agent to provide improved acute and/or chronic skin health benefits such as moisturisation and improved skin barrier function, immediate coverage of fine lines and wrinkles, and immediate improvement of tone and colour of the skin. The combination of the two components (a) and (b) comprising a self-tanning agent and a reactive skin care agent respectively enables the delivery to the skin of effective levels of both the self-tanning agent and the reactive skin care agent without the requirement for excessively high loading of the composition with either or both ingredients in order to ensure that appropriate levels of both ingredient are delivered to the skin when topically applied.

The reactive skin care agent of the present invention may comprise a nucleophilic skin care active. As used herein, the term "nucleophilic skin care active" includes materials, or their hydrolysis products, that react via nucleophilic addition to the carbon-oxygen double bond present on the self-tanning agent. Without wishing to be bound by theory, it is believes that this nucleophilic addition leads to a condensation reaction between the nucleophilic skin care active and the self-tanning agent, degrading the nucleophilic skin care active in the process, and generating an N-substituted imine or schiff base, which consequently go onto to take part in the remainder of a Maillard reaction to form coloured, typically brown, chromophores. Preferably the nucleophilic skin care active comprises vitamin $B_3$ compound or its derivatives, panthenol or its derivatives, dialkanol hydroxyproline compounds, hexamidine compounds, sugar amines or mixtures thereof.

A suitable nucleophilic skin care active for use in component (b) of the present invention comprises a vitamin $B_3$ compound or its derivatives. As used herein, "vitamin $B_3$ compound" includes compounds having the formula (II):

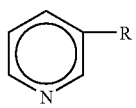

(II)

wherein R is —$CONH_2$ (i.e., niacinamide), —COOH (i.e., nicotinic acid) or —$CH_2OH$ (i.e., nicotinyl alcohol); derivatives thereof; and salts of any of the foregoing. Exemplary derivatives of the foregoing vitamin $B_3$ compounds include 'non-vasodilating' esters of nicotinic acid, nicotinyl amino acids, nicotinyl alcohol esters of carboxylic acids, nicotinic acid N-oxide and niacinamide N-oxide. Preferably, the compositions herein comprise niacinamide. As used herein, "non-vasodilating" means that the ester does not commonly yield a visible flushing response after application to the skin in the subject compositions. These levels of vitamin $B_3$ compound are preferred to deliver excellent benefits to the skin with regards to repairing skin barrier function. Vitamin $B_3$ compounds have been shown to have a breadth of cutaneous benefits, due to their known status as a precursor of nicotinamide cofactors such as NAD(H), NADP(H). The known benefits of niacinamide include upregulation of sphingolipid synthesis, including those ceramides critical to the formation of the lipid bilayer and so stratum corneum barrier integrity. Preferably the cosmetic kits herein comprise from 0.1% to 10%, more preferably from 0.5% to 5% vitamin $B_3$ compound or derivative by weight of the total composition.

Another nucleophilic skin care active suitable for use herein comprises panthenol or its derivatives. The panthenol and its derivatives include D-panthenol ([R]-2,4-dihydroxy-N-[3-hydroxypropyl)]-3,3-dimethylbutamide), DL-panthenol, calcium pantothenate, royal jelly, panthetine, pantotheine, panthenyl ethyl ether, pangamic acid, pyridoxin, pantoyl lactose and Vitamin B complex. More preferably, the composition herein comprises panthenol. The compositions of this invention may contain a safe and effective amount of the panthenol, such that the resultant composition is safe and effective for regulating skin texture. The panthenol derivative is preferably used in an amount of from about 0.1% to about 5%, more preferably from about 0.2% to about 3%.

A further nucleophilic skin care active suitable for use herein comprises dialkanol hydroxyproline compounds. The dialkanoyl hydroxyproline compounds suitable for use in the present invention correspond to those of the following chemical structure:

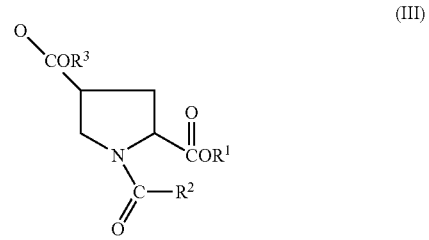

(III)

wherein $R^1$ comprises H, X, $C_1$-$C_{20}$ straight or branched alkyl,

X comprises metals (Na, K, Li, Mg, Ca) or amines (DEA, TEA);

$R^2$ comprises $C_1$-$C_{20}$ straight or branched alkyl;

$R^3$ comprises $C_1$-$C_{20}$ straight or branched alkyl.

The topical compositions of the present invention comprise a safe and effective amount of one or more dialkanoyl hydroxyproline compounds and their salts and derivatives. In the composition of the present invention, the dipalmitoyl hydroxyproline compounds preferably comprise from about 0.01 to 10%, more preferably from about 0.1 to 5%, more preferably still from about 0.1 to 2% by weight of the composition Suitable derivatives include but are not limited to esters, for example fatty esters, including, but not limited to tripalmitoyl hydroxyproline and dipalmityl acetyl hydroxyproline.

A particularly useful compound is dipalmitoyl hydroxyproline. As used herein, dipalmitoyl hydroxyproline" includes any isomers and tautomers of such and is commercially available under the tradename Sepilift DPHP® from Seppic, Inc. Further discussion of dipalmitoyl hydroxy proline appears in PCT Publication WO 93/23028. Preferably the dipalmitoyl hydroxyproline is the triethanolamine salt of dipalmitoyl hydroxyproline.

Another nucleophilic skin care active suitable for use herein comprises hexamidine compounds. The hexamidine compounds useful in the present invention correspond to those of the following chemical structure:

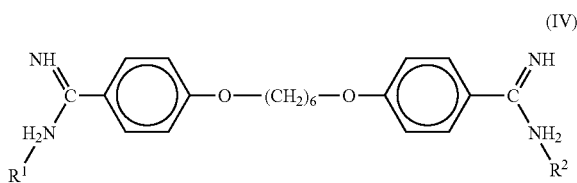

(IV)

wherein $R^1$ and $R^2$ comprise organic acids (e.g., sulfonic acids, etc.).

In the composition of the present invention, the hexamidine compound preferably comprises from about 0.001-10%, more preferably from about 0.01-5%, and most preferably from about 0.02-2.5%.

The topical compositions of the present invention optionally include a safe and effective amount of one or more of hexamidine compounds, its salts and its derivatives. As used herein, hexamidine derivatives includes any isomers and tautomers of hexamidine compounds including but not limited to organic acids and mineral acids, for example sulfonic acid, carboxylic acid etc.

Preferably, the hexamidine compounds include hexamidine diisethionate, commercially available as Elestab® HP100 from Laboratoires Serobiologiques (Pulnoy, France).

A further nucleophilic skin care active suitable for use herein comprise a sugar amine, which are also known as amino sugars. The sugar amine compounds useful in the present invention are described in PCT Publication WO 02/076423, and U.S. Pat. No. 6,159,485.

Preferably, the composition contains from about 0.01% to about 15%, more preferably from about 0.1% to about 10%, and most preferably from about 0.5% to about 5% by weight of the composition, of the sugar amine.

Sugar amines can be synthetic or natural in origin and can be used as essentially as pure compounds or mixtures of compounds (e.g., extracts from natural sources or mixtures of synthetic materials). Glucosamine is generally found in many shellfish and can also be derived from fungal sources. As used herein, "sugar amine" includes isomers and tautomers of such and its salts (e.g., HCl salt) and its derivatives and is commercially available from Sigma Chemical Co., St. Louis, Mo.

Examples of sugar amines that are useful herein include glucosamine, N-acetyl glucosamine, mannosamine, N-acetyl mannosamine, galactosamine, N-acetyl galactosamine, their isomers (e.g., stereoisomers), and their salts (e.g., HCl salt). Preferred for use herein are glucosamine, particularly D-glucosamine and N-acetyl glucosamine, particularly N-acetyl-D-glucosamine. Additionally, combinations of two or more sugar amines may be used. The topical compositions of the present invention also comprise a safe and effective amount of one or more glucosamine compounds. Most preferred for use herein is N-acetyl D-glucosamine.

Component (b) of the present invention may additionally comprise an auto-degradation catalyst. As used herein, the term "auto-degradation catalyst" includes materials that catalyse the auto-degradation of the self-tanning agents present in component (a). Without wishing to be bound by theory, it is believed that the auto-degradation catalysts destabilise the self-tanning agent herein by complexing with the self-tanning agent to form an unstable dicarbonyl intermediate that can polymerise with itself, or react with other materials present in the same phase via the remainder of a Maillard reaction to form coloured, typically brown, chromophores. Preferably, the auto-degradation catalyst includes salicylic acid or its derivatives, oxides of transition metals such as titanium, iron or zinc, or derivatives thereof, or mixtures thereof. As used herein, derivatives of transition metal oxides includes materials that comprise transition metal oxides in any form, non-limiting examples of which include transition metal oxides themselves and transition metal oxide-coated substrates such as interference pigments.

A suitable auto-degradation catalyst for use herein comprises salicylic acid or its derivatives. Salicylic acid derivatives include any 2, 3 or 4-OR substituted benzoic acid compound having the formula (V):

(V)

wherein R is selected from $C_1$-$C_6$ alkyl or $C_1$-$C_6$ acyl, preferably wherein R is selected from $C_2$-$C_3$ alkyl or $C_2$-$C_3$ acyl. Preferably, the compositions herein comprise salicylic aid. Preferably, the cosmetic kit of the present invention comprises up to 2% salicylic acid or its derivatives, more preferably from 1% to 2% by weight of the total composition.

Another auto-degradation catalyst suitable for use herein comprises transition metal oxides. Preferably, the transition metal oxides comprise oxides of titanium or derivatives thereof, oxides of iron or derivatives thereof, oxides of zinc or mixtures thereof. The materials may be pigmentary or sunscreen grades. Pigmentary grade materials are typically around 0.3-0.5 micron in size to maximise opacity. They can be coated or uncoated depending on the hydrophilic/hydrophobic nature of the phase they are to be incorporated into. Preferably, the pigmentary grade materials useful herein are uncoated as this makes them hydrophilic in nature and disperse well in water. Sunscreen grades of transition metal oxides are typically in the micronized form, having mean particulate sizes of from 10 to 50 nm. As stated above, the transition metal oxides may be present in a pure form, or as part of a coated substrate, such as metal oxide-coated mica. Non-limiting examples of these materials include the Prestige range of silver and gold by Eckart and Flamenco Summit Range such as Flamenco Summit Red, by Engelhard. Non-limiting examples of suitable commercially available pigmentary grade materials include materials available from Kobo, Warner Jenkinson and US Cosmetics. Suitable examples of sunscreen grade transition metal oxides include the MT series from Tayca or Tioveil CM from Uniqema (TiO2) and Z-Cote HP1 from BASF (ZnO). Where present, the transition metal oxides are typically present at levels of from 0.01% to 20%, more preferably from 0.5% to 10% by weight of the total composition.

Components (a) and (b) of the subject invention may be made into a wide variety of product forms such as are known in the art. These include, but are not limited to, lotions, creams, gels, sticks, sprays, ointments, pastes, mousses, aerosols and cosmetics (e.g., foundations, eye-makeup, pigmented or non-pigmented lip treatments, e.g., lipsticks, and the like). Components (a) and (b) may be made into the same or different product forms from one another. As previously indicated, the at least two components may be intended to be dispensed simultaneously and be mixed at the time of use, or to be applied sequentially, with one component being applied, followed by another. Where the two components are to be applied simultaneously, it is preferable that they are made in compatible product forms. Alternatively, where the two components are to be applied sequentially, the at least two components may be made in any combination of product forms known to one skilled in the art. In a preferred embodiment, the two components of the present invention are impregnated onto two halves of a substrate such as a wet-wipe or a foam-based substrate to allow simultaneous application.

The at least two components (a) and (b) of the present invention may be dispensed and applied to the skin at a ratio by weight of from 1:99 to 99:1. Preferably, the components are dispensed and applied to the skin at a ratio of from 20:80 to 80:20, more preferably from 40:60 to 60:40.

Preferably the pH of the at least two components is adjusted to limit the degradation of the ingredients therein. Preferably, the pH of component (a) of the present invention is from 3.0 to 5.0, more preferably from 3.5 to 4.5. The pH of component (b) may be from 2 to 9, dependent upon the reactive skin care agents present therein.

The components (a) and (b) of the present invention comprise a safe and effective amount of a dermatologically acceptable carrier within which the essential materials and optional other materials are incorporated to enable the essential materials and optional components to be delivered to the skin at an appropriate concentration. The carrier may be solid, semi-solid or liquid. Preferred carriers are substantially liquid. The type of carrier utilized in the present invention depends on the type of product form desired for the composition.

Preferred carriers comprise an emulsion comprising a hydrophilic phase and a hydrophobic phase. As is well known to one skilled in the art, the hydrophilic phase will be dispersed in the hydrophobic phase, or vice versa, to form respectively hydrophilic or hydrophobic dispersed and continuous phases, depending on the composition ingredients. The emulsion may be or comprise (e.g., in a triple or other multi-phase emulsion) an oil-in-water emulsion or a water-in-oil emulsion such as a water-in-silicone emulsion. The at least two components herein are preferably in the form of a water-in-oil or oil-in-water emulsion. More preferably the cosmetic compositions herein are oil-in-water emulsions wherein the composition comprises one or more oil phases in an aqueous continuous phase, each oil phase comprising a single oily component or a mixture of oily components in miscible or homogeneous form. Different oil phases contain different materials, or different combinations of materials, from each other. The total level of oil phase components in the compositions of the invention is typically from 0.1% to 60%, preferably from 1% to 30%, more preferably from 3% to 20% and most preferably from 5% to 15% by weight of the total composition.

Emulsions of the present invention also comprise a hydrophilic component, e.g., water or other hydrophilic diluent. The hydrophilic phase can thus comprise water, or a combination of water and one or more water soluble or dispersible ingredients. Hydrophilic components comprising a substantial amount of water are preferred. The composition preferably comprises from about 10% to about 95% of the hydrophilic diluent, more preferably 30% to 85%.

The hydrophilic phase may additionally comprise a humectant. Suitable humectants useful herein include polyhydric alcohols, sodium 2-pyrrolidone-5-carboxylate (NaPCA), amino acids and derivatives, guanidine; glycolic acid and glycolate salts (e.g. ammonium and quaternary alkyl ammonium); lactic acid and lactate salts (e.g. ammonium and quaternary alkyl ammonium); other alpha hydroxy acids such as malic acid, aloe vera in any of its variety of forms (e.g., aloe vera gel); hyaluronic acid, precursors and derivatives thereof (e.g., glucosamine and salt derivatives such as sodium hyaluronate); lactamide monoethanolamine; acetamide monoethanolamine; urea; and mixtures thereof. Preferred for use in the compositions of the present invention are polyhydric alcohols. If urea is to be used, it may only be present in component (b), as it is itself likely to react with and destabilise the self-tanning agent present in component (a).

Suitable polyhydric alcohols for use herein include polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, erythritol, threitol, pentaerythritol, xylitol, glucitol, mannitol, hexylene glycol, butylene glycol (e.g., 1,3-butylene glycol), hexane triol (e.g., 1,2,6-hexanetriol), trimethylol propane, neopentyl glycol, glycerine, ethoxylated glycerine and propoxylated glycerine. Preferred polyhydric alcohols of the present invention are polyhydric alcohols with 3 to 9 carbon atoms in the molecule. Examples include glycerine, butylene glycol, propylene glycol, dipropylene glycol, polyethylene glycol and derivatives thereof, hexane triol, ethoxylated glycerine and propoxylated glycerine, and mixtures thereof. More preferred for use in the present invention is glycerin. The compositions of the present invention comprise from about 5% to about 40% polyhydric alcohol, preferably from about 8% to about 15% by weight of the composition.

In preferred embodiments, the oil phase of either or both components preferably comprises oily materials such as a natural or synthetic oils selected from mineral, vegetable, and animal oils, fats and waxes, fatty acid esters, fatty alcohols, fatty acids and mixtures thereof. Preferred for use herein are for example, saturated and unsaturated fatty alcohols such as behenyl alcohol, cetyl alcohol and stearyl alcohol and hydrocarbons such as mineral oils or petrolatum.

The oil phase may additionally comprise an oil-soluble skin care active. Non-limiting examples of oil-soluble skin care actives suitable for use herein include ceramides, cholesterols, fatty acids, vitamin E or its dertivatives, or mixtures thereof. Non-limiting examples of commercially available blends of oil-soluble skin care actives suitable for use herein include SK Influx from Cosmoferm and Vitamin E acetate.

The present compositions may further comprise a silicone phase. The silicone phase can comprise one or more silicone components such as silicone fluids, gums, and mixtures thereof. The, or each, silicone phase generally comprises from 0.1% to 20%, preferably from 0.2% to 10%, more preferably from 0.3% to 5%, of the composition.

Silicone components can be fluids, including straight chain, branched and cyclic silicones. Suitable silicone fluids useful herein include silicones inclusive of polyalkyl siloxane fluids, polyaryl siloxane fluids, cyclic and linear polyalkylsiloxanes, polyalkoxylated silicones, amino and quaternary ammonium modified silicones, polyalkylaryl siloxanes or a polyether siloxane copolymer and mixtures thereof. The silicone fluids can be volatile or non-volatile.

The silicone components can also comprise silicone gums. The term "silicone gum" herein includes high molecular weight silicones having a weight average molecular weight in excess of about 200,000 and preferably from about 200,000 to about 4,000,000. Included are non-volatile polyalkyl and polyaryl siloxane gums. In preferred embodiments, a silicone oil phase comprises a silicone gum or a mixture of silicones including the silicone gum.

Useful herein are silicone/gum fluid blends. Preferred silicone-gum fluid blend based component for use in the compositions herein is a dimethiconol gum having a molecular weight of from 200,000 to 4,000,000 along with a silicone fluid carrier with a viscosity of 0.65 to 100 mm$^2 \cdot$s$^{-1}$. An example of this silicone component is Dow Corning Q2-1503 (85% 5 mm$^2 \cdot$s$^{-1}$ Dimethicone Fluid/15% Dimethiconol) and Dow Corning Q2-1501 available from Dow Corning.

The compositions of the present invention also include from about 0.1% to about 30%, by weight of the composition, of a silicone elastomer component. Preferably, the composition includes from about 1% to about 20%, more preferably from about 2% to about 10%, by weight of the composition, of the silicone elastomer component.

Suitable for use herein are silicone elastomers, which can be emulsifying or non-emulsifying crosslinked siloxane elastomers or mixtures thereof. No specific restriction exists as to the type of curable organopolysiloxane composition which can serve as starting material for the crosslinked organopolysiloxane elastomer.

The term "emulsifying," as used herein, means crosslinked organopolysiloxane elastomers having at least one polyoxyalkylene (e.g., polyoxyethylene or polyoxypropylene) unit. Preferred emulsifying elastomers herein include polyoxyalkylene modified elastomers formed from divinyl compounds, particularly siloxane polymers with at least two free vinyl groups, reacting with Si—H linkages on a polysiloxane backbone. Preferably, the elastomers are dimethyl polysiloxanes crosslinked by Si—H sites on a molecularly spherical MQ resin. Emulsifying crosslinked organopolysiloxane elastomer can notably be chosen from the crosslinked polymers described in U.S. Pat. Nos. 5,412,004; 5,837,793; and 5,811,487. In addition, an emulsifying elastomer comprised of dimethicone copolyol crosspolymer (and) dimethicone is available from Shin Etsu under the tradename KSG-21.

Advantageously, the non-emulsifying elastomers are dimethicone/vinyl dimethicone crosspolymers. Such dimethicone/vinyl dimethicone crosspolymers are supplied by a variety of suppliers including Dow Corning (DC 9040 and DC 9041), General Electric (SFE 839), Shin Etsu (KSG-15, 16, 18 [dimethicone/phenyl vinyl dimethicone crosspolymer]), and Grant Industries (GRANSIL™ line of elastomers). Cross-linked organopolysiloxane elastomers useful in the present invention and processes for making them are further described in U.S. Pat. No. 4,970,252; U.S. Pat. No. 5,760,116; U.S. Pat. No. 5,654,362. Additional crosslinked organopolysiloxane elastomers useful in the present invention are disclosed in Japanese Patent Application JP 61-18708, assigned to Pola Kasei Kogyo KK.

Commercially available elastomers preferred for use herein are Dow Corning's 9040 silicone elastomer blend, Shin Etsu's KSG-21, and mixtures thereof.

The topical compositions of the present invention include from about 1% to about 80%, by weight of the composition, of a suitable carrier for the for the crosslinked organopolysiloxane elastomer component described above. The carrier, when combined with the cross-linked organopolysiloxane elastomer particles of the present invention, serves to suspend and swell the elastomer particles to provide an elastic, gel-like network or matrix. The carrier for the cross-linked siloxane elastomer is liquid under ambient conditions, and preferably has a low viscosity to provide for improved spreading on the skin.

Preferred for use herein are organopolysiloxanes selected from the group consisting of polyalkylsiloxanes, alkyl substituted dimethicones, cyclomethicones, trimethylsiloxysilicates, dimethiconols, polyalkylaryl siloxanes, and mixtures thereof. More preferred for use herein are polyalkylsiloxanes and cyclomethicones. Preferred among the polyalkylsiloxanes are dimethicones. Commercially available examples are DC200 and DC245 series materials available from Dow Corning.

The topical compositions of the present invention preferably comprise emollient materials including branched chain hydrocarbons having an weight average molecular weight of from 100 to 15,000, preferably from 100 to 1000; compounds of formula VI:

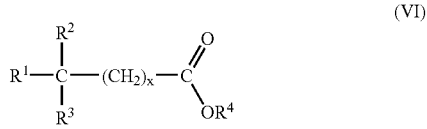

(VI)

wherein R$^1$ is selected from H or CH$_3$, R$^2$, R$^3$ and R$^4$ are independently selected from C$_1$-C$_{20}$ straight chain or branched chain alkyl, and x is an integer of from 1-20; and compounds having the formula VII:

(VII)

wherein R$^5$ is selected from optionally hydroxy or C$_1$-C$_4$ alkyl substituted benzyl and R$_6$ is selected from C$_1$-C$_{20}$ branched or straight chain alkyl; and mixtures thereof.

Suitable branched chain hydrocarbons for use herein include isododecane, isohexadecane, isoeicosane, isooctahexacontane, isohexapentacontahectane, isopentacontaoctactane, and mixture thereof. Suitable ester emollient materials of Formula (VI) include but are not limited to C12-15 alkyl benzoates.

Preferred emollients for use herein are isohexadecane, isononyl isononanoate, methyl isostearate, isopropyl isostearate, and mixtures thereof. A further emollient suitable for use in the composition of the present invention is petrolatum.

The emollient material is preferably present in the compositions at a level of from about 0.1% to about 10%.

The topical compositions of the present invention may comprise a wide variety of optional components, provided that such optional components are physically and chemically compatible with the essential components described herein, and do not unduly impair stability, efficacy or other use benefits associated with the compositions of the present invention. Optional components may be dispersed, dissolved or the like in the carrier of the present compositions.

The present compositions herein may comprise an emulsifier and/or surfactant, generally to help disperse and suspend the discontinuous phase within the continuous phase. For convenience hereinafter emulsifiers will be referred to under the term 'surfactants', thus 'surfactant(s)' will be used to refer to surface active agents whether used as emulsifiers or for other surfactant purposes such as skin cleansing.

Known or conventional surfactants can be used in the composition, provided that the selected agent is chemically and physically compatible with essential components of the composition, and provides the desired characteristics.

The compositions of the present invention preferably comprise from 0.05% to 15% of a surfactant or mixture of surfactants. The exact surfactant or surfactant mixture chosen will depend upon the pH of the composition and the other components present. Surfactants suitable for use herein include non-ionic, cationic, anionic, zwitterionic, amphoteric surfactants, or mixtures thereof.

Preferred surfactants are nonionic. Among the nonionic surfactants that are useful herein are those that can be broadly defined as condensation products of long chain alcohols, e.g. $C_{8-30}$ alcohols, with sugar or starch polymers, i.e., glycosides. Preferred examples include a mixture of cetearyl glucosides and cetearyl alcohols such as those commercially available as Montanov 68™ from Seppic and Emulgade PL68/50™ available from Henkel.

Other useful nonionic surfactants include the condensation products of alkylene oxides with fatty acids (i.e. alkylene oxide esters or diesters of fatty acids). Other nonionic surfactants are the condensation products of alkylene oxides with fatty alcohols (i.e. alkylene oxide ethers of fatty alcohols). Still other nonionic surfactants are the condensation products of alkylene oxides with both fatty acids and fatty alcohols [i.e. wherein the polyalkylene oxide portion is esterified on one end with a fatty acid and etherified (i.e. connected via an ether linkage) on the other end with a fatty alcohol]. Still other useful nonionic surfactants include polyhydroxy fatty acid amide surfactants, which are described in more detail in WO98/04241.

Another emulsifier useful herein are fatty acid ester blends based on a mixture of sorbitan or sorbitol fatty acid ester and sucrose fatty acid ester, the fatty acid in each instance being preferably $C_8$-$C_{24}$, more preferably $C_{10}$-$C_{20}$. The preferred fatty acid ester emulsifier is a blend of sorbitan or sorbitol $C_{16}$-$C_{20}$ fatty acid ester with sucrose $C_{10}$-$C_{16}$ fatty acid ester, especially sorbitan stearate and sucrose cocoate. This is commercially available from ICI under the name Arlatone 2121™.

Preferred among the nonionic surfactants are those selected from the group consisting of cetearyl glucosides, cetearyl alcohols, PEG-100 stearate, sorbitan stearate and mixtures thereof.

Emulsions of the present invention may include a silicone containing emulsifier or surfactant. A wide variety of silicone emulsifiers are useful herein. These silicone emulsifiers are typically organically modified organopolysiloxanes, also known to those skilled in the art as silicone surfactants. Useful silicone emulsifiers include dimethicone copolyols. Other examples include alkyl-modified dimethicone copolyols, i.e., compounds that contain $C_2$-$C_{30}$ pendant side chains. Still other useful dimethicone copolyols include materials having various cationic, anionic, amphoteric, and zwitterionic pendant moieties.

The compositions hereof, and especially the emulsions hereof, may contain a structuring agent. Structuring agents are particularly preferred in the oil-in-water emulsions of the present invention. Without being limited by theory, it is believed that the structuring agent assists in providing rheological characteristics to the composition which contribute to the stability of the composition. Preferred for use herein are for example, saturated and unsaturated fatty alcohols such as behenyl alcohol, cetyl alcohol and stearyl alcohol.

The compositions of the present invention can also comprise a thickening agent, preferably from about 0.1% to about 5%, more preferably from about 0.1% to about 3%, and most preferably from about 0.25% to about 2%, of a thickening agent. Non-limiting examples of thickening agents suitable for use herein include:

(i) Crosslinked Acrylate Copolymers: These polymers comprise a blend of a water soluble anionic acrylic monomer, a water-soluble non-ionic acrylate monomer and a bifunctional monomeric cross-linking agent. Suitable water-soluble anionic acrylic based monomers include acrylic acid, methacrylic acid and mixtures thereof. Suitable water-soluble non-ionic acrylate-based monomers include acrylamide, methacrylamide, N-vinyl pyrolidone, water-soluble hydroxy-substituted acrylic or methacrylic esters or mixtures thereof. Suitable bifunctional monomeric cross-linking agents include di, tri and tetraethylenically unsaturated materials such as methylene bis acrylamide, divinylpyrroline and allyl (meth) acrylate or mixtures thereof. Commercial examples of co-polymer compositions suitable for use herein include the co-polymer compositions commercially available from BASF Corp. under the tradename Luvigel™ EM and the co-polymer compositions available from CIBA Speciality Chemicals, Macclesfield, UK, under the tradename Salcare SC91™.

(ii) Hydroxyalkylacrylate polymers: Polymer comprises a monomer having a strongly acidic function, a neutral hydroxyethylacrylate monomer and a cross linking agent. The strongly acidic function of the monomer containing it is preferably a sulphonic acid function or a phosphonic acid function, partially or totally salified. Non-limiting examples of monomers having a strongly acidic function group suitable for use herein include partially or totally salified 2-methyl-2-[(1-oxo-2-propenyl)amino]-1-propanesulphonic acid, partially or totally salified styrene-sulfonic acid, or mixtures thereof. Non-limiting examples of the hydroxy alkyl acrylate neutral monomer suitable for use herein include 2-hydroxy-ethyl acrylate, 2,3-dihydroxypropyl acrylate, 2-hydroxy-ethyl methacrylate and 2,3-dihydroxypropyl methacry-late, or an ethoxylated derivative. Suitable cross linking agents are diethylenic or polyethylenic compounds, including ethylene glycol dimethacrylate, sodium diallyloxyacetate, ethylene glycol diacrylate, diallylurea, trimethylolpropane triacrylate, methylene bisacrylamide. Suitable examples of commercially available cross-linked anionic polyelectrolyte polymers includeSimulgel NS from Seppic Corporation (Fairfield, N.J.).

(iii) Polyacrylamide Polymers: Also useful herein are polyacrylamide polymers, especially anionic polyacrylamide/AMPS polymers including substituted branched or unbranched polymers. These polymers can be formed from a variety of monomers including acrylamide and methacrylamide which are unsubstituted or substituted with one or two alkyl groups (preferably $C_1$ to $C_5$). Preferred are acrylate amide and methacrylate amide monomers in which the amide nitrogen is unsubstituted, or substituted with one or two $C_1$ to $C_5$ alkyl groups (preferably methyl, ethyl, or propyl), for example, acrylamide, methacrylamide, N-methacrylamide, N-methylmethacrylamide, N,N-dimethylmethacrylamide, N-isopropylacrylamide, N-isopropylmethacrylamide, and N,N-dimethylacrylamide. Most preferred among these polyacrylamide/AMPS polymer is the anionic polymer given the CTFA designation polyacrylamide and isoparaffin and laureth-7, available under the tradename Sepigel 305 from Seppic Corporation (Fairfield, N.J.).

(iv) Natural Gum Thickeners: The at least two components of the present invention may further comprise a natural gum thickener. Preferably, component (a) comprises a natural gum thickener. It has been found that the rheology and stability of the present compositions can be suitably modified and improved by the addition of low levels of natural gum thickeners, without the compositions becoming too stringy, or tacky. Natural gum thickeners suitable for use herein include xanthan gum, guar gum or its derivatives, chitosan, alginates, carragenan, locust bean gum, sclerotium, pectin, starches or their derivatives, or mixtures thereof, preferably xanthan gum. Where present, the natural gum thickeners are preferably present at levels of from 0.05% to 3%, more preferably from 0.05% to 1%, more preferably still from 0.05% to 0.5% by weight of the component.

The compositions of the present invention may optionally include particulate materials. Particulate materials suitable herein include materials that are insoluble in both water and oil with a median particle size of from 1 μm to 50 μm. Preferably the compositions of the present invention comprise particulate materials having a refractive index of from about 1.3 to about 1.7, the particulate materials being dispersed in the composition and having a median particle size of from about 2 to about 30 μm. Suitable particulate materials are organic or organosilicone or inorganic. Preferred particles are free-flowing, solid, materials. By "solid" is meant that the particles are not hollow. The void at the centre of hollow particles can have an adverse effect on refractive index and therefore the visual effects of the particles on either skin or the composition. Suitable organic particulate materials include those made of polymethylsilsesquioxane, polyamide, polyethylene, polypropylene polyacrylonitrile, polyacrylic acid, polymethacrylic acid, polystyrene, polytetrafluoroethylene (PTFE) and poly (vinylidene chloride). Copolymers derived from monomers of the aforementioned materials can also be used. Inorganic materials include silica and boron nitride. Representative commercially available examples of useful particulate materials herein are Microthene FN510™, Tospearl 145™, Orgasol 2002™, Nylonpoly WL10™, Dry Flo™ or mixtures thereof. The compositions of the present invention can comprise from about 0.1% to about 5% by weight of particulate materials.

A further optional component may comprise sunscreening agents. Preferred among those sunscreens which are useful in the compositions of the invention are those selected from octylmethoxycinnamate, p-aminobenzoic acid, 2-phenylbenzimidazole-5-sulfonic acid, octocrylene, oxybenzone, homomenthyl salicylate, octyl salicylate, 4,4'-methoxy-t-butyldibenzoylmethane, 4-isopropyl dibenzoylmethane, 3-benzylidene camphor, 3-(4-methylbenzylidene) camphor, and mixtures thereof.

Generally, the sunscreens can comprise from about 0.5% to about 20% of the compositions useful herein. Exact amounts will vary depending upon the sunscreen chosen and the desired Sun Protection Factor (SPF). SPF is a commonly used measure of photoprotection of a sunscreen against erythema. See *Federal Register*, Vol. 43, No. 166, pp. 38206-38269, Aug. 25, 1978.

The cosmetic kits of the present invention are useful for imparting an artificial colour to the skin following topical application that is similar in intensity and hue to that generated by exposure to the sun. A wide range of quantities of the compositions of the present invention can be employed. Quantities of the final composition, which are typically applied per application, are, in mg final composition/cm$^2$ skin, from about 0.1 mg/cm$^2$ to about 20 mg/cm$^2$. A particularly useful application amount is about 0.5 mg/cm$^2$ to about 10 mg/cm$^2$.

EXAMPLES

Unless otherwise stated, all the following examples are formulated such as to be mixed at a ratio of 50:50 during application to generate a final composition. Each of components (a) and (b) have individually had their total ingredients summed to 100%.

Examples 1-3

Moisturising Cream Kits

| INGREDIENTS | EXAMPLE 1 Component (a) (w/w %) | EXAMPLE 1 Component (b) (w/w %) | EXAMPLE 2 Component (a) (w/w %) | EXAMPLE 2 Component (b) (w/w %) | EXAMPLE 3 Component (a) (w/w %) | EXAMPLE 3 Component (b) (w/w %) |
| --- | --- | --- | --- | --- | --- | --- |
| DEIONISED WATER | QS | QS | QS | QS | QS | QS |
| GLYCERINE | 10.0 | 10.0 | 5.0 | 5.0 | 15.0 | 15.0 |
| NIACINAMIDE | 4.0 | — | — | — | 2.0 | — |
| PANTHENOL | 1.0 | — | 6.0 | — | 2.0 | — |
| VITAMIN E ACETATE | 0.25 | 0.25 | 0.25 | 0.25 | 0.25 | 0.25 |
| ISOHEXADECANE | 3.0 | 3.0 | 3.0 | 3.0 | 3.0 | 3.0 |
| ISOPROPYLISOSTEARATE | 1.50 | 1.50 | 1.50 | 1.50 | 1.3 | 1.50 |
| COCONUT OIL FRACTIONATED | 0.2 | 0.2 | 0.2 | 0.2 | — | — |
| PETROLATUM | 2.0 | 2.0 | 2.0 | 2.0 | 2.0 | 2.0 |
| SIMUGEL NS[3] | — | 1.5 | — | 1.5 | — | 2.0 |
| LUVIGEL EM[4] | 2.0 | — | — | — | 2.5 | — |
| SEPIGEL 305[5] | — | — | 1.5 | — | — | — |
| XANTHAN GUM | 0.1 | 0.1 | 0.1 | 0.2 | 0.1 | 0.2 |

-continued

| INGREDIENTS | EXAMPLE 1 Component (a) (w/w %) | EXAMPLE 1 Component (b) (w/w %) | EXAMPLE 2 Component (a) (w/w %) | EXAMPLE 2 Component (b) (w/w %) | EXAMPLE 3 Component (a) (w/w %) | EXAMPLE 3 Component (b) (w/w %) |
|---|---|---|---|---|---|---|
| SORBITAN STEARATE | — | — | — | — | 0.9 | — |
| STEARYL ALCOHOL | 0.6 | 0.6 | 0.6 | 0.6 | 0.55 | 0.6 |
| CETYL ALCOHOL | 0.5 | 0.5 | 0.5 | 0.5 | 0.8 | 0.5 |
| BEHENYL ALCOHOL | 0.4 | 0.4 | 0.4 | 0.4 | — | 0.4 |
| PEG-100 STEARATE | 0.1 | 0.1 | 0.1 | 0.1 | 0.1 | 0.1 |
| STEARIC ACID | 0.1 | — | 0.1 | — | 0.1 | — |
| SODIUM HYDROXIDE | 0.01 | — | 0.01 | — | 0.04 | — |
| EMULGADE[6] | 0.2 | 0.2 | 0.2 | 0.2 | 0.2 | 0.2 |
| NYLONPOLY WL10[7] | — | 1.0 | — | 1.0 | — | 1.0 |
| DRY FLO PLUS[8] | 0.5 | 1.0 | 0.5 | 1.0 | 0.5 | 1.0 |
| MICROTHENE[9] | — | — | 0.5 | — | — | — |
| FLAMENCO SUMMIT RED[10] | 2.0 | — | — | — | 2.0 | — |
| TITANIUM DIOXIDE | — | — | 0.5 | — | — | — |
| DHA[11] | — | 1.5 | — | 1.8 | — | 5.0 |
| ERYTHRULOSE[12] | — | — | — | 0.6 | — | — |
| ETHYL PARABEN | 0.15 | 0.15 | 0.15 | 0.15 | 0.15 | 0.15 |
| PROPYL PARABEN | 0.07 | 0.07 | 0.07 | 0.07 | 0.07 | 0.07 |
| DISODIUM EDTA | 0.1 | 0.1 | 0.1 | 0.1 | 0.1 | 0.1 |
| BENZYL ALCOHOL | 0.25 | 0.25 | 0.25 | 0.25 | 0.25 | 0.25 |
| DC 1503 | 1.0 | 1.0 | 1.0 | 1.0 | 1.0 | 1.0 |
| PERFUME | 0.2 | 0.2 | 0.2 | 0.2 | 0.2 | 0.2 |

[1] SK Influx: Supplied by Goldschmidt AG, Goldschmidtstrasse 100, D-45127 Essen, Germany.
[2] Tocopherol Nicotinate: Supplied by Ennagram UK Ltd, Edelman House, 1238 High Road, Whetstone, London.
[3] Simugel NS: Supplied by Seppic, 75 Quai D'Orsay, Paris
[4] Luvigel EM: BASF Plc, PO Box 4-Earl Road, Cheadle Hulme, Cheshire SK8 6QG
[5] Sepigel 305: Supplied by Seppic, 75 Quai D'Orsay, Paris
[6] Emulgade: Supplied by Cognis Deutchland GmbH, Paul-Thomas Strasse 56, D-40551 Dusseldorf, Germany.
[7] Nylonpoly WL10: Supplier Optima Chemicals, Unit 17, Chiltern Business Village, Arundel Road, Uxbridge, Middlesex, UB8 2SN
[8] Dry Flo: Supplied by National Starch Chemical Company, 10, Finderne Avenue, Bridgewater, NJ 08807, USA
[9] Microthene: Supplied by Equistar Chemicals, 1221 McKinney Street, Suite 700, Houston, TX 77252-2583
[10] Flamenco Summit Red: Supplied by Engelhard P&A Europe, Emrikweg 18, NL-2031 BT Haarlem, Netherlands.
[11] DHA: Supplied by Merck GmBH, Frankfurter Strasse 250, 64293 Darmstadt, Germany.
[12] Erythrulose: Supplied by Pentapharm, Engelgasse 109, 4002 Basel, Switzerland.

The compositions are made as follows:

A water phase is prepared by admixing all water-soluble ingredients (including xanthan gum), except DHA and Erythrulose (if included), in water and heating to 80° C. A second premix is prepared by admixing of the oil-soluble ingredients except the silicone oil (DC1503) and heating also to 80° C. The oil phase is added to the water phase and sheared to form an emulsion.

The emulsion is cooled to 60° C. and the polymeric thickener is then added. At 45-50° C. the benzyl alcohol and DC1503, and particles (if included) are added and the resulting product is sheared to ensure particle dispersion, de-agglomeration and homogeneity. The composition can then be cooled to below 40° C. and DHA, Erythrulose (if included) and perfume can be added.

Example 4

Disposable Fluid Applicator Kit

The disposable applicator already comprises the fluid to be dispensed, so does not require addition of any fluid prior to use. Example 1 is taken and at least one of the phases is incorporated within a rupturable dosing reservoir capable of containing and dispensing the cream. The second phase may be contained in a similar manner or within an alternative type of reservoir ie. foam etc. The reservoirs are then enclosed within a flow control layer comprising an apertured film to allow the cream to be dispensed onto the skin when pressure is applied. Preferably, additional batting, sponge or foam is added to aid handleability and a fluid impermeable layer incorporated to prevent flow of product onto the hands.

Example 5

Moisturising Gel Kit

| INGREDIENTS | Component (a) (w/w %) | Component (b) (w/w %) |
| --- | --- | --- |
| DEIONISED WATER | QS | QS |
| GLYCERINE | 5.0 | 5.0 |
| NIACINAMIDE | 4.0 | — |
| PANTHENOL | 1.0 | — |
| SIMUGEL NS[3] | 3.0 | 3.0 |
| XANTHAN GUM | 0.2 | 0.2 |
| DHA[11] | — | — |
| ERYTHRULOSE[12] | — | — |
| ETHYL PARABEN | 0.15 | 0.15 |
| PROPYL PARABEN | 0.07 | 0.07 |
| DISODIUM EDTA | 0.1 | 0.1 |
| BENZYL ALCOHOL | 0.25 | 0.25 |
| PERFUME | 0.2 | 0.2 |

The compositions are made as follows:

The gel is made by dissolving the preservatives, niacinamide and DHA (if included) into a glycerine/water and panthenol pre-mix. Mixing should be done with a Lightin' mixer with a 3-blade paddle propeller. When the ingredients have dissolved xanthan gum is added and allowed to hydrate. The polymeric thickener is then added, whilst mixing at a moderate speed, and the gel forms. The product can then be prepared for packaging.

Example 6

Line Minimising Moisturiser Kit

| INGREDIENTS | Phase 1 (w/w %) | Phase 2 (w/w %) |
| --- | --- | --- |
| DEIONISED WATER | QS | QS |
| GLYCERINE | 10.0 | 10.0 |
| NIACINAMIDE | 2.0 | — |
| PANTHENOL | 2.0 | — |
| DC9040[13] | 25.0 | 25.0 |
| DC245[14] | 15.0 | 15.0 |
| DC AMS C30 Wax[15] | 3.0 | 3.0 |
| KSG21[15] | 10.0 | 10.0 |
| DHA[11] | — | 2.0 |
| PROPYL PARABEN | 0.25 | 0.25 |
| DISODIUM EDTA | 0.1 | 0.1 |
| PHENOXYETHANOL | 0.25 | 0.25 |
| PERFUME | 0.1 | 0.1 |

[13,14] and [15]Supplied by Dow Corning, Kings Court, 185 Kinds Rd, Reading, Berks, RGI 4EX
[14]KSG21: Supplied by Shin Etsu, Bolderweg 32, 1332 AV, Almere, The Netherlands The compositions are made as follows:

A water phase is prepared by admixing all water soluble ingredients, except DHA (if included) and phenoxyethanol, in water and heating to 50° C. Once the phase is clear, it is cooled and the phenoxyethanol and DHA (if included) are added. A second premix is prepared by heating the DC245 to 80° C. When at temperature the wax is added and allowed to melt. Once fully molten the DC9040 is added and the mixture is allowed to cool whilst mixing under low shear continuously. Once below 40° C., the perfume is incorporated into the silicone phase and then the water phase is added and sheared to form an emulsion. The product is then suitable for packing into an appropriate container.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A cosmetic kit comprising at least two separated components (a) and (b) intended to be mixed at the time of use to generate a final composition or to be applied successively wherein component (a) comprises a self-tanning agent comprising an α-hydroxyaldehyde conforming to the formula;

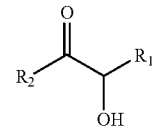

wherein $R_1$ is H, $CH_2OH$, $CHOHCH_2OH$, $CH(OH)CH(=O)$, $CH(OCH_3)CH(=O)$, $CH(NH_2)CH(=O)$, or $CH(NH\text{-Phenyl})CH(=O)$; and $R_2$ is H or $CH_2OH$; and component (b) comprises a reactive skin care active comprising vitamin $B_3$ compound or its derivatives, panthenol or its derivatives, dialkanol hydroxyproline compounds, hexamidine compounds, sugar amines or mixtures thereof.

2. The cosmetic kit according to claim 1 comprising from about 0.01% to about 10% self-tanning agent by weight of the final composition.

3. The cosmetic kit according to claim 1 wherein the α-hydroxyaldehyde comprises dihydroxyacetone, erythrulose, or mixtures thereof.

4. The cosmetic kit according to claim 3 wherein the α-hydroxyaldehyde comprises dihydroxyacetone.

5. The cosmetic kit according to claim 1 further comprising an auto-degradation catalyst.

6. The cosmetic kit according to claim 5 wherein the auto-degradation catalyst comprises transition metal oxides, salicylic acid or its derivatives, or mixtures thereof.

7. The cosmetic kit according to claim 6 wherein the transition metal oxide comprises oxides of titanium, iron, zinc, or mixtures thereof.

8. The cosmetic kit according to claim 1 wherein the reactive skin care active comprises niacinamide, panthenol, hexamidine, or mixtures thereof.

9. The cosmetic kit according to claim 1 wherein each of the components (a) and (b) are in the form of an emulsion.

10. The cosmetic kit according to claim 1 wherein component (a) has a pH of from about 3.5 to about 4.5.

11. The cosmetic kit according to claim 1 wherein component (a) additionally comprises a thickener.

12. The cosmetic kit according to claim 11 wherein said thickener comprises an alkyl acrylate co-polymer, a natural gum, a polyacrylamide, or mixtures thereof.

13. The cosmetic kit according to claim 12 wherein component (a) comprises a hydroxyethylacrylate copolymer.

14. The cosmetic kit according to claim 1 wherein the at least two components comprise from about 5% to about 40% humectant by weight of the total composition.

15. The cosmetic kit according to claim 1 comprising a package comprising at least two separate compartments.

16. The cosmetic kit according to claim 15 wherein one of the two compartments contains component (a) and the or another compartment comprises component (b).

17. A method of imparting colour to skin comprising applying to the skin a cosmetic kit according to claim 1.

* * * * *